(12) United States Patent
Chavas et al.

(10) Patent No.: US 11,320,649 B2
(45) Date of Patent: May 3, 2022

(54) OBJECTIVE, CAMERA AND SYSTEM ADAPTED FOR OPTOGENETICS COMPRISING SUCH OBJECTIVE

(71) Applicants: GENSIGHT BIOLOGICS, Paris (FR); Sorbonne Université, Paris (FR); Centre National de la Recherche Scientifique, Paris (FR); INSTITUT NATIONAL DE LA SANTE ET DE LA RECHERCHE MEDICALE (INSERM), Paris (FR)

(72) Inventors: Joël Chavas, Orsay (FR); Guillaume Chenegros, Trappes (FR); Charlie Galle, Paris (FR)

(73) Assignees: GENSIGHT BIOLOGICS, Paris (FR); Sorbonne Université, Paris (FR); Centre National de la Recherche Scientifique, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 325 days.

(21) Appl. No.: 16/622,987

(22) PCT Filed: Jun. 28, 2018

(86) PCT No.: PCT/EP2018/067487
§ 371 (c)(1),
(2) Date: Dec. 16, 2019

(87) PCT Pub. No.: WO2019/002509
PCT Pub. Date: Jan. 3, 2019

(65) Prior Publication Data
US 2021/0149188 A1 May 20, 2021

(30) Foreign Application Priority Data
Jun. 28, 2017 (EP) ..................... 17305805

(51) Int. Cl.
*G02B 3/00* (2006.01)
*G02B 27/00* (2006.01)
(Continued)

(52) U.S. Cl.
CPC .......... *G02B 27/0068* (2013.01); *G02B 3/14* (2013.01); *A61F 2/16* (2013.01)

(58) Field of Classification Search
CPC ............... G02B 1/06; G02B 3/12; G02B 3/14
(Continued)

(56) References Cited

U.S. PATENT DOCUMENTS

2005/0259157 A1    11/2005  Keiichi
2006/0028734 A1*    2/2006  Kuiper ................. G02B 3/14
                                                              359/676
(Continued)

FOREIGN PATENT DOCUMENTS

CN          1705901         12/2005
CN         104856643         8/2015
(Continued)

OTHER PUBLICATIONS

Edward S Boyden et al., "Millisecond-timescale, genetically targeted optical control of neural activity", Nature Neuroscience, vol. 8, No. 9, Aug. 14, 2005.
(Continued)

*Primary Examiner* — James C. Jones
(74) *Attorney, Agent, or Firm* — Zaretsky Group PC; Howard Zaretsky (57) ABSTRACT

The present invention concerns an objective (10) for imaging an object field of view of 10° onto an imager (12), the objective (10) comprising in order of the propagating direction: —a first lens unit (U1) comprising several lenses, the first lens unit (U1) having a positive first focal length and a first dimension inferior to 15 millimeters, —a bending
(Continued)

mirror (M) adapted to bend at a 90° angle, —a liquid lens (LL), and —a second lens unit (U2) comprising several lenses, the second lens unit (U2) having a positive second focal length and a second dimension, the ratio between the first focal length and the second focal length being comprised between 1.0 and 2.0 and the ratio between the first dimension and the second dimension being superior or equal to 2.

14 Claims, 2 Drawing Sheets

(51) Int. Cl.
*G02B 3/14* (2006.01)
*A61F 2/16* (2006.01)

(58) Field of Classification Search
USPC .......................................................... 359/642
See application file for complete search history.

(56) References Cited

U.S. PATENT DOCUMENTS

| | | | |
|---|---|---|---|
| 2009/0091844 A1 | 4/2009 | Jannard et al. | |
| 2011/0002043 A1 | 1/2011 | Seo et al. | |

FOREIGN PATENT DOCUMENTS

| | | |
|---|---|---|
| JP | S61/275817 | 12/1986 |
| JP | S61275817 | 12/1986 |
| JP | 2005/352240 | 12/2005 |
| JP | 2005352240 | 12/2005 |
| WO | 2004/038480 | 5/2004 |
| WO | 2004038480 | 5/2004 |
| WO | 2007024391 | 3/2007 |
| WO | 2008022772 | 2/2008 |
| WO | 2009127705 | 10/2009 |
| WO | 2013071231 | 5/2013 |

OTHER PUBLICATIONS

John Martin Barrett et al., "Optogenetic approaches to retinal prosthesis", Visual Neuroscience, (2014), 31, pp. 345-354, Cambridge University Press, https://www.cambridge.org/core, Aug. 6, 2014.

Brent Asrican et al., "Next-generation transgenic mice for optogenic analysis of neural circuits", Frontiers in Neural Circuits, www.frontiersi vol. 7, Article 160, pp. 1-24, Nov. 26, 2013.

Busskamp et al., "Optogenetic therapy for retinitis pigmentosa", Gene Therapy advance online publication, Macmillan Publishers Limited, www.nature.com/gt, Oct. 13, 2011.

Karl Deisseroth et al., "Optogenetics", Nat Methods. Jan. 2011 ; 8(1): 26-29.

International Search Report for PCT/EP/2018,067487, European Patent Office, dated Aug. 6, 2018.

Nathan C Klapoetke et al., "Independent Optical Excitation of Distinct Neural Populations", Nat Methods. Mar. 1, 2014 ; 11(3): 338-346.

Dae Yeong Lee et al., "Implantation of Modular Photovoltaic Subretinal Prosthesis", Ophthalmic Surg Lasers Imaging Retina. Feb. 2016 ; 47(2): 171-174.

Tai-Chi Lin et al., "Retinal prostheses in degenerative retinal diseases", Journal of the Chinese Medical Association 78 (2015) 501-505.

Georg Nagel et al., "Channelrhodopsin-2, a directly light-gated cation-selective membrane channel", PNAS, www.pnas.org. vol. 100, No. 24, pp. 13940-13945, Nov. 25, 2003.

Hendrik P. N. Scholl et al., "Emerging therapies for inherited retinal degeneration", Science Translational Medicine, 8, 368rv6, Dec. 7, 2016.

International Written Opiniont for PCT/EP/2018/067487, European Patent Office, dated Aug. 6, 2018.

\* cited by examiner

OBJECTIVE, CAMERA AND SYSTEM ADAPTED FOR OPTOGENETICS COMPRISING SUCH OBJECTIVE

TECHNICAL FIELD OF THE INVENTION

The invention relates to an objective for imaging an object field of view of 10° onto an imager. The invention also concerns an associated camera and an associated system adapted for optogenetics.

BACKGROUND OF THE INVENTION

The retina is composed of photoreceptors, which are highly specialized neurons that are responsible for photosensitivity of the retina by phototransduction, i.e. the conversion of light into electrical and chemical signals that propagate a cascade of events within the visual system, ultimately generating a representation of world. In the vertebrate retina, phototransduction is initiated by activation of light-sensitive receptor protein, rhodopsin.

Photoreceptor loss or degeneration, such as in case of retinitis pigmentosa (RP) or macular denementation (MD), severely compromises, if not completely inhibits, phototransduction of visual information within the retina. Loss of photoreceptor cells and/or loss of a photoreceptor cell function are the primary causes of diminished visual acuity, diminished light sensitivity, and blindness.

Several therapeutic approaches dedicated to retinal degenerative diseases are currently in development, including gene therapy, stem cell therapy, optogenetics, and retinal prostheses (Scholl et al., 2016, Science Translational Medicine, 8 (368), 368rv6).

For example it has been proposed to restore photosensitivity of the retina of a subject by controlling activity of defined populations of neurons without affecting other neurons in the brain by gene- and neuroengineering technology termed optogenetics. In contrast to traditional gene therapy that attempts to replace or repair a defective gene or bypass the genetic defect through correction of the protein deficiency or dysfunction, optogenetic approaches can be used to endow normally non-photosensitive cells in the retina with the ability to respond to light, thus restoring useful vision to the patient. Unlike retinal chip implants that provide extracellular electrical stimulation to bipolar or ganglion cells, optogenetics-based therapies stimulate the cells from inside the cell.

Optogenetics (Deisseroth. Nat Methods 8 (1): 26-9, 2011) refers to the combination of genetics and optics to control well-defined events within specific cells of living tissue. Optogenetics It consists in (i) genetically modifying target cells in order to render them sensitive to light by the expression of exogenous photoreactive proteins in cellular membrane and (ii) providing illuminating device able to provide light to said photoreactive proteins.

Examples of exogenous photoreactive proteins are provided in WO2007024391, WO2008022772 or WO2009127705 which describe the use of opsin genes derived from plants and microbial organisms (e.g. archaebacteria, bacteria, and fungi) encoding light-activated ion channels and pumps (e.g. channelrhodopsin-2 [ChR2]; halorhodopsin [NpHR]), engineered for expression in mammalian neurons and which can be genetically targeted into specific neural populations using viral vectors. When exposed to light with appropriate wavelength, action potentials can be triggered in opsin-expressing neurons conferring thereby light sensitivity to these cells. Similarly, WO2013071231 discloses new channelrhodopsins, Chronos and Chrimson, which have different activation spectra from one another and from the state of the art (e.g., ChR2/VChR1), and allow multiple and distinct wavelengths of light to be used to depolarize different sets of cells in the same tissue, by expressing channels with different activation spectra genetically expressed in different cells, and then illuminating the tissue with different colors of light.

Optogenetics is an extremely powerful tool for selective neuronal activation/inhibition which can, for example, be used to restore neural functions in living animals, including humans (Boyden et al., 2005, *Nature Neuroscience* 8 (9): 1263-68), particularly in the eye (Busskamp et al., 2012, *Gene Therapy* 19 (2): 169-75).

Nevertheless, it has been shown that selected wavelengths of light shall be close to the optimal wavelengths of the photoreactive proteins (Nagel et al. 2003, *Proceedings of the National Academy of Sciences* 100 (24): 13940-45, Klapoetke et al. 2014, *Nature Methods* 11 (3): 338-46) and that these photoreactive proteins have a very low sensitivity to light (Asrican et al. 2013, *Front Neural Circuits*, 2013, 7:160; Busskamp et al. 2012, *Gene Therapy* 19 (2): 169-75). Therefore in order to obtain minimum level of protein activation by light, the intensity of light received by the target cell or protein shall be above a minimum value (Barrett et al., 2014, *Visual Neuroscience* 31 (4-5): 345-354). As a consequence, an external device providing sufficient irradiance at the right wavelength is mandatory.

Alternatively, it has been proposed to restore at least partially vision in these patients with visual prosthesis systems. These systems are comprising a retina implant which are helpful tools for at least partially re-establishing a modest visual perception and a sense of orientation for blind and visually impaired users by exploiting said fact that although parts of the retinal tissue have degenerated most of the retina may remain intact and may still be stimulated directly by light dependent electrical stimuli. Typically, retina implant is implanted into the patient's eye, effecting electrical excitation of the remaining neuronal cells upon light stimulation. When being stimulated, these remaining neuronal cells convey the artificially induced electrical impulses to the visual part of the brain through the optic nerve.

Retinal implants can be broadly divided into two categories: epi- and sub-retinal (Lin et al., 2015, Retinal prostheses in degenerative retinal diseases, J Chin Med Assoc.; 78(9): 501-5). Epi-retinal devices are placed on or near the inner surface of the retina, i.e. the side of the retina which is first exposed to incident light and along which the nerve fibers of the ganglion cells pass on their way to the optic nerve. Epi-retinal implants typically comprise a chip with a plurality of pixel elements capable of receiving an image projected by an extraocular device (typically a camera and a microelectronic circuit for decoding incident light) on the retina through the lens of the eye, for converting the image into electrical signals and for further conveying the signals into electrical stimuli via a plurality of stimulation electrodes to stimulate the retinal cells adjacent the chip, in order to reconstruct or improve vision of blind or partially blind patients. In contrast, sub-retinal devices are placed under the retina, between the retina and the underlying retinal pigment epithelium or other deeper tissues. Currently available sub-retinal technologies rely on the implantation of a single, rigid and typically planar chip. It has been further shown that it is desirable to be able to implant more than one chip in order to cover a large visual field (Lee et al. (2016).

Implantation of Modular Photovoltaic Subretinal Prosthesis. *Ophthalmic Surgery, Lasers and Imaging Retina,* 47(2), 171-174).

Retinal prostheses and optogenetic therapies rely on two main components. The first component engineered on the retina provides light sensitivity through transducing photons into electrochemical signals: the implant in retinal prosthesis system and light-gated ion channel protein genetically introduced in the retinal cells in optogenetic therapies. A second component is required to encode visual information (usually acquired with a camera or array of photodiodes) and to translate it in an input signal required by the former component. In retinal prostheses, the input signal is an electrical current delivered by a matrix of active electrodes or a pulse of light capable of activating passive components. In optogenetics gene therapy, the input signal which is delivered is a pulse of light at the appropriate intensity and wavelength required to activate the optogenetic protein in a defined spatio-temporal manner.

Regardless of the approach used to restore light sensitivity, a stimulating device able to encode visual information in real time is required.

SUMMARY OF THE INVENTION

The invention aims at providing an objective adapted to be embedded in a stimulating device used in a system to restore partially vision on blind subjects affected by Retinis Pigmentosa.

For this, thanks to his studies, the Applicant has expressed the requirements to be fulfilled by such objective.

First, the objective should have a reduced size, notably inferior to 25 millimeters.

Moreover, the objective has to provide a sufficient resolution, in particular inferior to 30 micrometers (μm).

Furthermore, the objective should provide with an object field of view of 10°.

The objective should also provide with a tunable focal length enabling to image objects situated above 40 centimeters.

To this end, it is proposed an objective for imaging an object field of view of 10° onto an imager provided with more than 100 pixels, a propagating direction being defined for the objective, the objective comprising in order of the propagating direction a first lens unit, a bending mirror, a liquid lens and a second lens unit. The first lens unit comprises a plurality of lenses, the first lens unit having a first focal length and a first dimension, the first focal length being positive and the first dimension being inferior to 15 millimeters. The bending mirror is adapted to bend at a 90° angle. The second lens unit comprises a plurality of lenses, the second lens unit having a second focal length and a second dimension, the second focal length being positive, the ratio between the first focal length and the second focal length being comprised between 1.0 and 2.0 and the ratio between the first dimension and the second dimension being superior or equal to 2.

Thanks to the presence of the bending mirror and the limitation on the first dimension, the objective has a reduced size.

The use of a liquid lens provides with an adjustable focal length enabling to image objects situated above 40 centimeters.

In addition, the specific architecture with two lens units with positive focal lengths, the ratio between the first focal length and the second focal length being comprised between 1.0 and 2.0 and the ratio between the first dimension and the second dimension being superior or equal to 2 enables to obtain an image quality which provides a sufficient resolution for an object field of view of 10°.

The above-mentioned benefits of the architecture of the objective as previously described are obtained regardless the definition of lens sequences and aperture stops.

According to further aspects of the invention which are advantageous but not compulsory, the objective might incorporate one or several of the following features, taken in any technically admissible combination:

the material of each lens belonging to the first lens unit and the second lens unit is chosen among only two distinct materials.

This feature enables to reduce the number of lenses involved while keeping a sufficient image quality. As a result, such feature also contributes to obtaining an objective with a reduced size.

the number of lenses of the first lens unit and the number of lenses of the second lens unit is inferior or equal to four.

This feature reduces the number of lenses which are present in the objective, which notably reduce the size of the objective.

at least one of the first lens unit and of the second lens unit comprises a biconvex lens and a concave meniscus.

Such feature enables to limit the number of lenses which keeping a sufficient image quality. This also results in an objective easier to manufacture.

each lens belonging to the first lens unit and the second lens unit is chosen among only a biconvex lens or a meniscus lens.

Such feature enables to limit the number of lenses which keeping a sufficient image quality. This also results in an objective easier to manufacture.

the first lens unit comprises at least two lenses, the first lenses in the propagating direction being a convergent lens and a divergent lens, the ratio in absolute value between the focal length of the divergent lens and the focal length of the convergent lens being comprised between 1.8 and 2.2.

Such feature enables to obtain in an easier way a good image quality. This also results in an objective with a reduced size.

the first focal length is comprised between 30.0 millimeters and 40.0 millimeters.

Such feature limits the focal length of the first lens unit. This results in an objective with a reduced size.

the second focal length is comprised between 20.0 millimeters and 35.0 millimeters.

Such feature limits the focal length of the second lens unit. This results in an objective with a further reduced size.

the second lens unit comprises, in the order of the propagating direction, a divergent lens and a convergent lens, the ratio in absolute value between the focal length of the divergent lens and the focal length of the convergent lens being comprised between 1.8 and 3.6.

The presence of such feature improves the quality of the image.

the first lens of the first lens unit has an entrance focal length and the last lens of the second lens unit has an exit focal length, the ratio between the exit focal length and the entrance focal length in absolute value being comprised between 0.7 and 1.0.

Such feature enables to obtain a good image quality over the whole field of 10°.

the first lens unit consists of three lenses.

Such feature enables to limit the number of lenses which keeping a sufficient image quality. This also results in an objective easier to manufacture.

the second lens unit consists of two lenses.

Such feature enables to limit the number of lenses which keeping a sufficient image quality. This also results in an objective easier to manufacture.

The specification also relates to a camera comprising an imager with more than 100 pixels and an objective as previously described.

It is also proposed a system adapted for optogenetics comprising a camera as previously described.

The above-mentioned system adapted to optogenetics is at least in part intended to be implanted in the eye of a patient. In particular, the camera of the system is intended to be implanted in the eye of the patient.

This may lead that the system has to respect quality and safety standards in order to be implanted in the eye. Moreover, this may lead to delimit structurally the system in terms of size and form in order to be implanted in the eye.

BRIEF DESCRIPTION OF THE DRAWINGS

The invention will be better understood on the basis of the following description which is given in correspondence with the annexed figures and as an illustrative example, without restricting the object of the invention. In the annexed figures.

GENERAL DESCRIPTION OF THE OBJECTIVE

Figure 1:
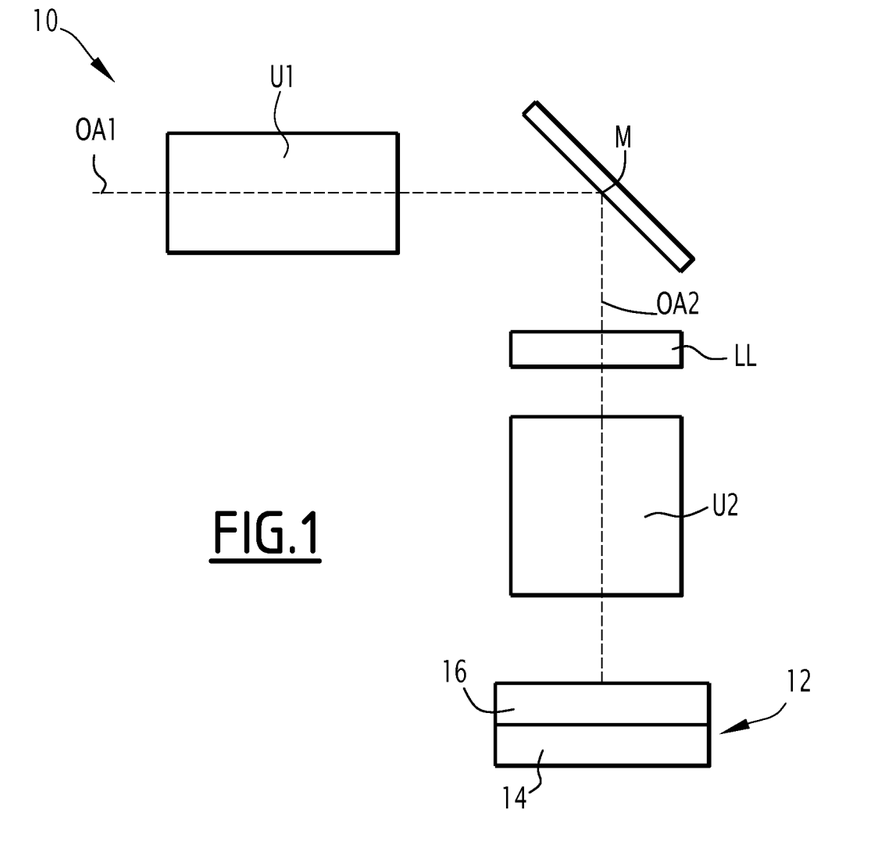
FIG. 1 shows schematically an objective and an imager, the objective comprising a first lens unit and a second lens unit.

An objective 10 and an imager 12 are represented schematically on FIG. 1.

The objective 10 is adapted to image an object field of view of 10° onto the imager 12.

A propagating direction Z is defined for the objective 10. The propagating direction Z is defined as the optical axis of each optical element that is part of the objective.

The objective 10 comprises in order of the propagating direction Z a first lens unit U1, a bending mirror M, a liquid lens LL and a second lens unit U2.

The first lens unit U1 comprises a plurality of lenses.

The number of lenses of the first lens unit U1 is inferior or equal to four.

The material of each lens belonging to the first lens unit U1 is chosen among only two distinct materials.

For instance, two distinct materials are N-BK7 and N-SF11.

The first lens unit U1 has a first focal length $f_{U1}$ and a first dimension $D_{U1}$.

The first focal length $f_{U1}$ is positive.

According to an example, the first focal length $f_{U1}$ is comprised between 30.0 millimeters (mm) and 40.0 mm.

The first dimension $D_{U1}$ is inferior to 15 mm.

The bending mirror M is adapted to bend at a 90° angle.

A first optical axis OA1 is defined for the first lens unit U1 and the second optical axis OA2 is defined for the liquid lens LL and the second lens unit U2.

The expression "the bending mirror M is adapted to bend at a 90° angle" means that the first optical axis OA1 and the second optical axis OA2 are perpendicular.

In the example of FIG. 1, the bending mirror M is a flat mirror which is arranged at 45° with relation to the first optical axis OA1 and the second optical axis OA2.

The liquid lens LL is adapted to change its focal length upon application of a voltage.

The change of focal length of the liquid lens renders the objective 10 adapted to image objects situated at more than 40 centimeters from the first lens unit U1.

The second lens unit U2 comprising a plurality of lenses.

The number of lenses of the second lens unit U2 is inferior or equal to four.

The material of each lens belonging to the second lens unit U2 is chosen among only two distinct materials.

For instance, two distinct materials are N-BK7 and N-SF11.

The second lens unit U2 has a second focal length $f_{U2}$ and a second dimension $D_{U2}$.

The second focal length $f_{U2}$ is positive.

The ratio between the first focal length $f_{U1}$ and the second focal length $f_{U2}$ is named the first ratio R1. This can be expressed mathematically as:

$$R1 = \frac{f_{U1}}{f_{U2}}$$

The first ratio R1 is comprised between 1.0 and 2.5. Mathematically, this means that:

$$1.0 \leq R1 \leq 2.5$$

As a specific example, the second focal length $f_{U2}$ is comprised between 20.0 mm and 35.0 mm.

The ratio between the first dimension $D_{U1}$ and the second dimension $D_{U2}$ is named the second ratio R2. This can be expressed mathematically as:

$$R2 = \frac{D_{U1}}{D_{U2}}$$

The second ratio R2 is superior or equal to 2. Mathematically, this means that:

$$R2 \geq 2$$

The second ratio R2 is inferior or equal to 3. Mathematically, this means that:

$$R2 \leq 3$$

Figure 2:
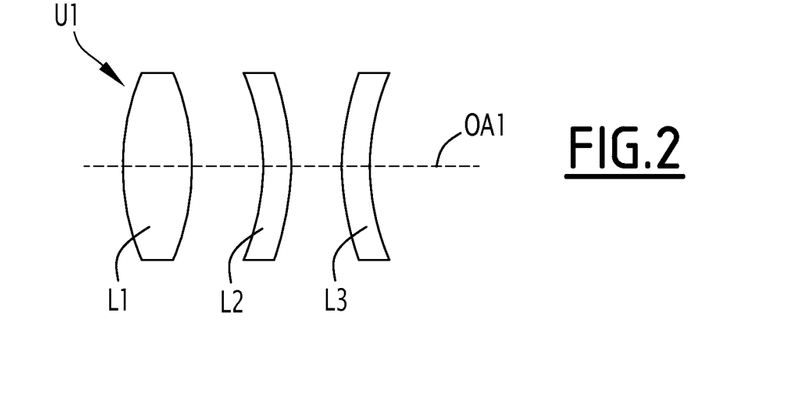
FIG. 2 shows a schematic view of the first lens unit of FIG. 1.

A specific example of first lens unit U1 is shown on FIG. 2.

In such case, the first lens unit U1 consists of three lenses.

In order of the propagating direction, the first lens of the first lens unit U1 is named first lens L1, the second lens of the first lens unit U1 is named second lens L2 and the third lens of the first lens unit U1 is named third lens L3.

The first lens L1 is a convergent lens.

The first lens L1 has a focal length $f_{L1}$.

The focal length $f_{L1}$ is the entrance focal length of the objective.

In addition, the first lens L1 is a biconvex lens.

By definition, a biconvex lens is a lens whose both surfaces are convex.

In this specific example, the first lens L1 is an equiconvex lens with means that both surfaces have the same radius of curvature.

The second lens L2 is a divergent lens.

The second lens L2 has a focal length $f_{L2}$.

The second lens L2 is a meniscus, which is a lens with one convex and one concave side. Such kind of meniscus is also named convex-concave lens.

The second lens L2 is, in this case, a negative meniscus.

The ratio in absolute value between the focal length $f_{L2}$ of the second lens L2 and the focal length $f_{L1}$ of the first lens L1 is named third ratio R3.

The third ratio R3 is comprised between 1.8 and 2.2.

Mathematically, this means that:

$$1.8 \leq R3 \leq 2.2$$

The third lens L3 is a divergent lens.

The third lens L3 has a focal length $f_{L3}$.

The third lens L3 is a meniscus.

The third lens L3 is, in this case, a positive meniscus.

Figure 3:
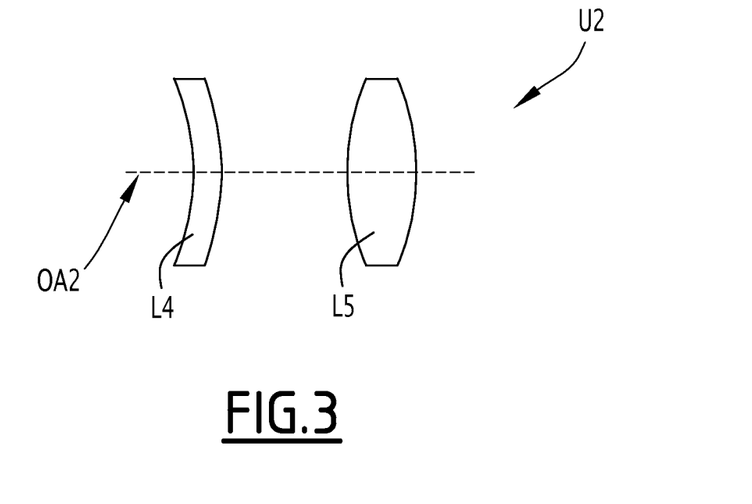
FIG. 3 shows a schematic view of the second lens unit of FIG. 1.

A specific example of second lens unit U2 is shown on FIG. 3.

In such case, the second lens unit U2 consists of two lenses.

In order of the propagating direction, the first lens of the second lens unit U2 is named fourth lens L4 and the second lens of the second lens unit U2 is named fifth lens L5.

The fourth lens L4 is a convergent lens.

The fourth lens L4 has a focal length $f_{L4}$.

The fourth lens L4 is a meniscus.

The fourth lens L4 is, in this case, a negative meniscus.

The fifth lens L5 is a divergent lens.

The fifth lens L5 has a focal length $f_{L5}$.

The focal length $f_{L5}$ of the fifth lens L5 is the exit focal length of the objective.

In the specific example, the fifth lens L5 is a biconvex lens.

More precisely, the fifth lens L5 is an equiconvex lens.

In another variant, the fifth lens L5 is a meniscus, notably a positive meniscus.

The ratio in absolute value between the focal length of the fifth lens L5 and the focal length of the fourth lens L4 is named the fourth ratio R4. This can be expressed mathematically as:

$$R4 = \left|\frac{f_{L5}}{f_{L4}}\right|$$

The fourth ratio R4 is comprised between 1.8 and 3.6.

Mathematically, this means that:

$$1.8 \leq R4 \leq 3.6$$

The ratio between the exit focal length and the entrance focal length in absolute value is named the fifth ratio R5.

In the specific case of FIGS. 2 and 3, the fifth ratio R5 is the ratio between the focal length $f_{L5}$ of the fifth lens L5 and the focal length $f_L$ of the first lens L1 in absolute value.

This can be expressed mathematically as:

$$R5 = \left|\frac{f_{L5}}{f_{L1}}\right|$$

The fifth ratio R5 is comprised between 0.7 and 1.0.

Mathematically, this means that:

$$0.7 \leq R5 \leq 1.0$$

The imager 12 is a set of an array of pixels 14 and a cover glass 16.

The array of pixels 14 comprises more than 100 pixels

In the specific example, the array of pixels 14 is an array of 304 pixels per 240 pixels.

The array of pixels 14 is, for instance, made in a CMOS technology.

The cover glass 16 is a plane-parallel plate.

The operating of the objective 10 in relation to the imager 12 is now described.

Any object in the field of view of the objective 10 situated at more than 40 centimeters from the first lens unit U1 is imaged on the array of pixels 14.

More precisely, the object emits a ray whose wavelength is in the visible range which passes successively through the first lens L1, the second lens L2, the third lens L3. This ray is then reflected by the bending mirror M and passes through the liquid lens LL and then the second lens unit U2, that is the fourth lens L4 and the fifth lens L5. The ray then propagates to the cover glass and is then collected by one pixel of the array of pixels 14.

This happens for each ray emitted by the object and more generally for each imaged object when the scene is imaged by the objective 10 in cooperation with the imager 12.

The obtained optical performances of such objective 10 are detailed in the specific examples which are described in the section named "description of specific embodiments".

It appears from this section that the objective provides with a reduced size and no use of mechanical apparatus for moving the lens, which results in an objective easier to implement. The objective also enables to provide a sufficient resolution. Furthermore, the objective provides with an object field of view of 10°. The objective also provides with an adjustable focal length enabling to image objects situated at more than 40 centimeters. Therefore, the objective 10 and the imager 12 enable to constitute a camera which is suitable for be embedded in a stimulating device used in a system to restore partially vision on bling subjects affected by Retinis Pigmentosa.

In other words, such camera is adapted to be part of a system adapted for optogenetics.

Figure 4:
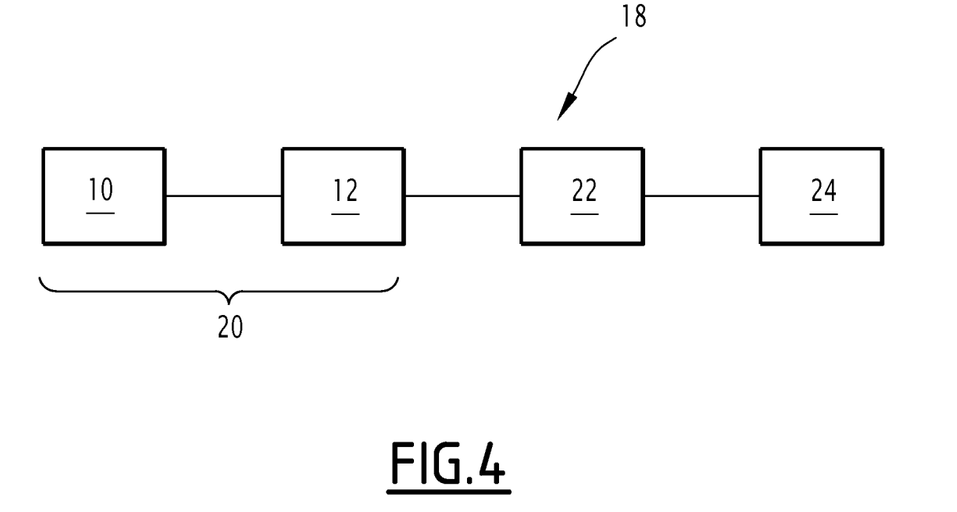
FIG. 4 illustrates a system adapted for optogenetics comprising the elements of FIG. 1.

An example of stimulating device 18 incorporating the objective 10 and the imager 12 is represented on FIG. 4. In such context, the set of the objective 10 and the imager 12 is a camera 20 which is a visual frontend.

The stimulating device 18 also comprises a controller 22 and a projecting unit 24.

The imager 12 is a QVGA ATIS (Asynchronous Time-based Images Sensor) neuromorphic silicon retina. Rather than sending frames at specific temporal intervals, each pixel of the imager 12 asynchronously sends an event encoding its coordinates as soon as it undergoes a local change of light. Events also trigger a dedicated pixel-based circuitry integrating light through time to compute a corresponding light intensity level. Each pixel therefore behaves asynchronously and in parallel with the others, without having to wait for a frame to transmit information. Each pixel sends information only when something new happens locally.

This translates to a low-latency, bandwidth-efficient encoding scheme, which shares the same properties as its biological counterparts; it is in fact possible to replicate in-vitro responses of retinal ganglions cells using this representation. Moreover, as pixels only send changes of information, redundancy is kept low, with obvious benefits for the subsequent processing layers. This approach contrasts with the traditional method of sending frames and provides fast, data-driven contrast detection at a wide range of illuminations.

The use of this imager 14 offers several advantages. In the case of photoreceptors restoration, the imager 14 provides fast, high-dynamic range grey level information. In the case of retinal ganglions cells activation, the imager 14 provides a preprocessed contour or event signal over a wide intensity range. The imager 14 temporal resolution also matches the one of the human retina. Projecting at low temporal resolutions impacts behavioral performance when observing moving stimuli in everyday tasks such as judging speeds, counting objects or discriminating numbers.

The projecting unit 24 is a Texas Instrument LightCrafter, controlling a light source and a DLP3000 Digital Micromirror Device (DMD). The DMD comprises a 608×684 array of mirrors that can switch every 0.7 millisecond (ms) between two discrete angular positions named ON and OFF, with the ON position reflecting the incoming light towards the target. Processed events are encoded by setting the corresponding mirror ON. Grey levels are encoded in the form of a Pulse Width Modulation.

The processing unit consists of an ARM-based embedded Linux system running an event-based filtering chain. The system communicates with a FPGA board handling the low level management of the imager 14 and of the DMD through a PCI express link and is abstracted in a Linux driver. Information received from the visual sensor is processed by a filtering pipeline and then sent to the DMD for projection. This filter pipeline handles the noise reduction, the size of the retinal area to be illuminated and the light pulse dynamics for each pixel, so as to comply with the electro-physiological properties of the genetically introduced ion channels. The filtering pipeline also handles the algorithms used to stimulate different types of neurons.

In such case, the projecting unit 24 and the controller 22 constitutes a device for illuminating an object with a controlled light intensity, the light intensity being controlled when the light intensity fulfills a plurality of conditions to be fulfilled, the plurality of conditions comprising a condition relative to the intensity at a given time and a condition relative to the dose during a period of time, the device comprising a light source adapted to produce a beam whose intensity does not fulfill at least one of the conditions to the fulfilled. The device comprises a photodiode adapted to measure the intensity of an incident beam and an optical system adapted to convey the light from an entrance to at least one exit, the light source, the photodiode and the optical system being arranged so that the device has two distinct configurations, an operating configuration in which a first portion of the light emitted by the light source is conveyed to the object, and a second portion of the light emitted by the light source is conveyed to the photodiode and a control configuration in which, in normal operating, no light produced by the light source is sent to object nor to the photodiode. The device also comprises a controller adapted to control the value of the first portion based on the intensity measured on the photodiode when the device is in the control configuration and based on the conditions to be fulfilled.

According to a specific embodiment, one condition to be fulfilled is that the light intensity at any given time be inferior or equal to a maximum intensity, one condition to be fulfilled is that the light intensity at any given time be superior or equal to a minimum intensity and one condition to be fulfilled is that the dose during the period of time be inferior or equal to a maximum value.

Furthermore, the optical system may comprise a plurality of reflectors, each reflector having three positions, a first position in which the reflector reflects the incident beam towards the object, a second position in which the reflector reflects the incident beam towards a photodiode and a third position in which the reflector reflects the incident beam neither to the object nor to the photodiode, the controller being adapted to command the position of each reflector, the device being in the operating configuration when the controller commands each reflector to be in the first position or in the second position and the device being in the control configuration when each reflector is commanded to be in the third position.

The controller may further be adapted to deduce the number of reflectors to be moved in the first position based on the intensity measured on the photodiode when the device is in the control configuration and based on the conditions to be fulfilled and commanding the deduced number of mirrors to move in the first position.

In a specific the light source is a matrix of light sources, each light source having two states, an unfed state in which the light source emits no light and a fed state in which the source emits light, the controller being adapted to control the state of each light source.

As a specific example, a plane to be illuminated is defined for the object and wherein at least one of the light source and the optical system is such that the several independent spatial areas illuminated by different levels of intensity of light can be defined in the plane to be illuminated when the device is in the operating configuration.

Furthermore, the optical system may comprise optical components ensuring that the point spread function be inferior to 30 μm, preferably inferior to 25 μm to the system output. As a specific example, the optical system comprises a system adapted for correcting optical aberrations, the system adapted for correcting optical aberrations being adjustable. For instance, the system is adapted for correcting optical aberrations is a liquid lens.

The embodiments and alternative embodiments considered here-above and also described in the section "detailed description of specific embodiments" can be combined to generate further embodiments of the invention.

DETAILED DESCRIPTION OF SPECIFIC EMBODIMENTS

Three embodiments are described in more details in what follows.

Subsequently, numerical data of optic constituting the objective of each embodiment are given in tables 1, 4 and 7. In the numerical data, the name of the optic is given as well as the unit to which the optic belongs, its nature, the value of the first radius $R_{in}$, the value of the second radius $R_{out}$, the thickness $D_{in\text{-}out}$ of the optic, the material of the optic, the focal length of the optic and its position.

The nature of an optic is, for a lens, the nature of the lens (biconvex, meniscus or other).

The value of the first radius $R_{in}$ is the value of the radius of the first surface of the optic which is impacted by the incoming ray, which is the entrance radius of the considered optic.

Similarly, the value of the second radius $R_{out}$ is the value of the second surface of the optic which is impacted by the incoming ray, which is the exit radius of the considered optic.

The thickness $D_{in\text{-}out}$ of the optic is the distance between the first surface (the entrance surface) and the second surface (the exit surface) of the considered optic. The thickness is the distance measured along the optical axis defined for the optic.

The focal length is obtained based on the first radius $R_{in}$, the second radius $R_{out}$, the thickness $D_{in\text{-}out}$ of the optic and the optical index of the material.

The position is the optic is the distance with the previous optic. More precisely, the position is the distance between the exit surface of the previous optic and the entrance surface of the considered optic. This distance is measured along the optical axis. This explains why there is no position for the first lens L1. Indeed, there is no reference for the first lens L1.

From the values obtained on tables 1, 4 and 7, numerical values characterizing the objective are deduced. The deduced numerical data of optic constituting the objective of each embodiment are given in tables 2, 5 and 8. More precisely, the deduced numerical data of optic is the first focal length $f_{U1}$, the first dimension $D_{U1}$, the second focal length $f_{U2}$, the second dimension $D_{U2}$, the first ratio R1, the second ratio R2, the third ratio R3, the fourth ratio R4 and the fifth ratio R5.

The first focal length $f_{U1}$ is obtained based on the focal lengths of the first lens L1, the second lens L2 and the third lens L3 and on the relative position of these lenses L1, L2 and L3 using, for example, a Gullstrand law.

The first dimension $D_{U1}$ corresponds to the sum of the thickness of the first lens L1, the distance between the first lens L1 and the second lens L2, the thickness of the second lens L2, the distance between the second lens L2 and the third lens L3 and the thickness of the third lens L3.

The second focal length $f_{U2}$ is obtained based on the focal lengths of the fourth lens L4, the fifth lens L5 and on the relative position of these lenses L4 and L5 using, for example, a Gullstrand law.

The second dimension $D_{U2}$ corresponds to the sum of the thickness of the fourth lens L4, the distance between the fourth lens L4 and the fifth lens L5 and the thickness of the fifth lens L5.

As a reminder, the first ratio R1 is the ratio between the first focal length $f_{U1}$ and the second focal length $f_{U2}$; the second ratio R2 is the ratio between the first dimension $D_{U1}$ and the second dimension $D_{U2}$; the third ratio R3 is the ratio in absolute value between the focal length $f_{L2}$ of the second lens L2 and the focal length $f_{L1}$ of the first lens L1; the fourth ratio R4 is the ratio in absolute value between the focal length $f_{L4}$ of the fourth lens L4 and the focal length $f_{L5}$ of the fifth lens of L5, and the fifth ratio R5 is the ratio in absolute value between the focal length $f_{L1}$ of the first lens L1 and the focal length $f_{L5}$ of the fifth lens L5.

The optical performances for each of the embodiment can be found respectively in tables 3, 6 and 9.

In each of these tables, the values of the modulation transfer function (MTF) is given for 30 lines per mm on-axis and off-axis (at the extremity of the imaged field of view) are given for a distance of the object to the objective 10 equal to 40 cm and a distance corresponding to infinity. The corresponding values of the root mean square (RMS) radius of the spot size are given.

Embodiment 1

The embodiment 1 was simulated thanks to a ray-tracing simulator. Such embodiment 1 only requires three specific lenses, which are the lenses L2, L3 and L4. The other optics are commercially available.

For instance, the first lens L may correspond to the reference SLB-15B-20PM from OptoSigma (registered trademark), the fifth lens may correspond to the reference #63-665 from Edmund Optics (registered trademark) and the liquid lens to the reference A58N0 from Varioptic (registered trademark).

TABLE 1

Numerical data of the objective in the first embodiment

| Optic | Unit | Nature | $R_{in}$ (mm) | $R_{out}$ (mm) | $D_{in\text{-}out}$ (mm) | Material | Focal length (mm) | Position (mm) |
|---|---|---|---|---|---|---|---|---|
| L1 | U1 | Biconvex lens | 20.76 | −20.76 | 4.8 | N-BK7 | 20.9 | — |
| L2 | U1 | Negative meniscus | −17.8 | −41.7 | 2.5 | N-SF11 | −41.5 | 1 |
| L3 | U1 | Positive meniscus | 8.11 | 6.0 | 4.5 | N-BK7 | −163.2 | 0.504 |
| mirror | | | | | | | | 5.94 |
| LL | | Liquid lens | — | — | 3.45 | — | variable | 6.9 |
| L4 | U2 | Negative meniscus | −7.95 | −10.2 | 1.8 | N-SF11 | −70.8 | 2 |
| L5 | U2 | Biconvex lens | 20.24 | −20.24 | 2.5 | N-BK7 | 20.0 | 1 |
| Cover glass | | | | | | | | 2.6 |

The index of N-BK7 is 1.5168 and the Abbe number is 64.17.
The index of N-SF11 is 1.7847 and the Abbe number is 25.68.

The previous results enable to obtain deduced values which are given in the following table:

TABLE 2

Deduced numerical data of the objective in the first embodiment

| | Parameters | | | | | | | | |
|---|---|---|---|---|---|---|---|---|---|
| | $f_{U1}$ (mm) | $D_{U1}$ (mm) | $f_{U2}$ (mm) | $D_{U2}$ (mm) | R1 | R2 | R3 | R4 | R5 |
| Value | 37.25 | 13.30 | 23.70 | 5.3 | 1.57 | 2.51 | 1.98 | 3.54 | 0.95 |

With the embodiment 1, the following optical performances are obtained:

TABLE 3

Optical performance of the objective in the first embodiment

| Parameters | MTF (%) at 30 lp/mm at 40 cm | MTF (%) at 30 lp/mm at infinity | Spot size at 40 cm (μm) | Spot size at Infinity (μm) |
|---|---|---|---|---|
| Value on axis | 62 | 75 | 6.5 | 5 |
| Value off axis | 27 | 45 | 11 | 8.75 |

These optical performances show that the objective 10 according to the first embodiment is compliant with the desired requirements, which are:
having a reduced size,
a sufficient resolution,
having an object field of view of 10°, and
providing with an adjustable focal length enabling to image objects situated at more than 40 centimeters.

Embodiment 2

The second embodiment was simulated thanks to a ray-tracing simulator. Such second embodiment only requires four specific lenses, which are the lenses L2, L3, L4 and L5. The other optics are commercially available.

For instance, the liquid lens may correspond to the reference A58N0 from Varioptic (registered trademark).

TABLE 4

Numerical data of the objective in the second embodiment

| Optic | Unit | Nature | $R_{in}$ (mm) | $R_{out}$ (mm) | $D_{in-out}$ (mm) | Material | Focal length (mm) | Position (mm) |
|---|---|---|---|---|---|---|---|---|
| L1 | U1 | Biconvex lens | 22 | −22 | 4.8 | N-BK7 | 22.1 | — |
| L2 | U1 | Negative meniscus | −18.8 | −39.8 | 2.5 | N-SF11 | −47.9 | 1 |
| L3 | U1 | Positive meniscus | 8.85 | 6.85 | 4.5 | N-BK7 | −251.3 | 0.504 |
| mirror | | | | | | | | 5.94 |
| LL | | Liquid lens | — | — | 3.45 | — | variable | 6.9 |
| L4 | U2 | Negative meniscus | −8.4 | −14.0 | 1.8 | N-SF11 | −31.2 | 2 |
| L5 | U2 | Positive meniscus | 16.0 | −17 | 2.5 | N-BK7 | 16.3 | 1 |
| Cover glass | | | | | | | | 2.6 |

This results in the following table:

TABLE 5

Deduced numerical data of the objective in the second embodiment

| | Parameters | | | | | | | | |
|---|---|---|---|---|---|---|---|---|---|
| | $f_{U1}$ (mm) | $D_{U1}$ (mm) | $f_{U2}$ (mm) | $D_{U2}$ (mm) | R1 | R2 | R3 | R4 | R5 |
| Value | 35.80 | 13.30 | 26.10 | 5.3 | 1.37 | 2.51 | 2.16 | 1.90 | 0.74 |

With the embodiment 2, the following optical performances are obtained:

TABLE 6

Optical performance of the objective in the second embodiment

| Parameters | MTF (%) at 30 lp/mm at 40 cm | MTF (%) at 30 lp/mm at infinity | Spot size at 40 cm (μm) | Spot size at Infinity (μm) |
|---|---|---|---|---|
| Value on axis | 68 | 88 | 6.65 | 2.7 |
| Value off axis | 28 | 18 | 12.7 | 14 |

These optical performances show that the objective 10 according to the second embodiment is compliant with the desired requirements, which are:
having a reduced size,
a sufficient resolution,
having an object field of view of 10°, and
providing with an adjustable focal length enabling to image objects situated at more than 40 centimeters.

Embodiment 3

The third embodiment was simulated thanks to a ray-tracing simulator. Such second embodiment only requires four specific lenses, which are the lenses L1, L2, L3 and L4. The other optics are commercially available.

For instance, the liquid lens may correspond to the reference A58N0 from Varioptic (registered trademark).

TABLE 7

Numerical data of the objective in the third embodiment

| Optic | Unit | Nature | $R_{in}$ (mm) | $R_{out}$ (mm) | $D_{in-out}$ (mm) | Material | Focal length (mm) | Position (mm) |
|---|---|---|---|---|---|---|---|---|
| L1 | U1 | Biconvex lens | 19.0 | −24.3 | 4.8 | N-BK7 | 21.4 | — |
| L2 | U1 | Negative meniscus | −20.75 | −52.6 | 2.5 | N-SF11 | −45.2 | 1 |
| L3 | U1 | Positive meniscus | 9.5 | 7.205 | 4.5 | N-BK7 | −173.9 | 0.504 |
| mirror | | | | | | | | 5.94 |
| LL | | Liquid lens | — | — | 3.45 | — | variable | 6.9 |
| L4 | U2 | Negative meniscus | −8 | −11 | 1.8 | N-SF11 | −50.8 | 2 |
| L5 | U2 | Biconvex lens | 19.3 | −19.3 | 2.5 | N-BK7 | 19.1 | 1 |
| Cover glass | | | | | | | | 2.6 |

This results in the following table:

TABLE 8

Deduced numerical data of the objective in the third embodiment

| | Parameters | | | | | | | |
|---|---|---|---|---|---|---|---|---|
| | $f_{U1}$ (mm) | $D_{U1}$ (mm) | $f_{U2}$ (mm) | $D_{U2}$ (mm) | R1 | R2 | R3 | R4 | R5 |
| Value | 36.60 | 13.30 | 25.15 | 5.3 | 1.46 | 2.51 | 2.11 | 2.66 | 0.89 |

With the embodiment 3, the following optical performances are obtained:

TABLE 9

Optical performance of the objective in the third embodiment

| Parameters | MTF (%) at 30 lp/mm at 40 cm | MTF (%) at 30 lp/mm at infinity | Spot size at 40 cm (μm) | Spot size at Infinity (μm) |
|---|---|---|---|---|
| Value on axis | 73 | 83 | 6.5 | 4.4 |
| Value off axis | 29 | 49 | 11 | 9.2 |

These optical performances show that the objective 10 according to the second embodiment is compliant with the desired requirements, which are:
having a reduced size,
a sufficient resolution,
having an object field of view of 10°, and
providing with an adjustable focal length enabling to image objects situated at more than 40 centimeters.

The invention claimed is:

1. An objective for imaging an object field of view of 10° onto an imager provided with more than 100 pixels, a propagating direction being defined for the objective, the objective comprising in order of the propagating direction:
a first lens unit comprising a plurality of lenses, the first lens unit having a first focal length and a first dimension, the first focal length being positive and the first dimension being inferior to 15 millimeters;
a bending mirror adapted to bend at a 90° angle;
a liquid lens; and
a second lens unit comprising a plurality of lenses, the second lens unit having a second focal length and a second dimension, the second focal length being positive, the ratio between the first focal length and the second focal length being comprised between 1.0 and 2.0 and the ratio between the first dimension and the second dimension being superior or equal to 2.

2. The objective according to claim 1, wherein the material of each lens belonging to the first lens unit and the second lens unit is chosen among only two distinct materials.

3. The objective according to claim 1, wherein the number of lenses of the first lens unit and the number of lenses of the second lens unit is inferior or equal to four.

4. The objective according to claim 1, wherein at least one of the first lens unit and of the second lens unit comprises a biconvex lens and a concave meniscus.

5. The objective according to claim 1, wherein each lens belonging to the first lens unit and the second lens unit is chosen among only a biconvex lens or a meniscus lens.

6. The objective according to claim 1, wherein the first lens unit comprises at least two lenses, the first lenses in the propagating direction being a convergent lens and a divergent lens, the ratio in absolute value between the focal length of the divergent lens and the focal length of the convergent lens being comprised between 1.8 and 2.2.

7. The objective according to claim 1, wherein the first focal length is comprised between 30.0 millimeters and 40.0 millimeters.

8. The objective according to claim 1, wherein the second focal length is comprised between 20.0 millimeters and 35.0 millimeters.

9. The objective according to claim 1, wherein the second lens unit comprises, in the order of the propagating direction, a divergent lens and a convergent lens, the ratio in absolute value between the focal length of the divergent lens and the focal length of the convergent lens being comprised between 1.8 and 3.6.

10. The objective according to claim 1, wherein the first lens of the first lens unit has an entrance focal length and the last lens of the second lens unit has an exit focal length, the ratio between the exit focal length and the entrance focal length in absolute value being comprised between 0.7 and 1.0.

11. The objective according to claim 1, wherein the first lens unit consists of three lenses.

12. The objective according to claim 1, wherein the second lens unit consists of two lenses.

13. A camera comprising an imager with more than 100 pixels and an objective according to claim 1.

14. A system adapted for optogenetics comprising a camera according to claim 13.

\* \* \* \* \*